United States Patent
Coqueron et al.

(10) Patent No.: US 8,283,349 B2
(45) Date of Patent: Oct. 9, 2012

(54) FUNGICIDE N-(3-PHENYLPROPYL) CARBOXAMIDE DERIVATIVES

(75) Inventors: Pierre-Yves Coqueron, Lyons (FR); Rüdiger Fischer, Pulheim (DE); Oliver Gaertzen, Köln (DE); Marie-Claire Grosjean-Cournoyer, Curis Au Mont d'or (FR); Benoît Hartmann, Sainte Foy-les-Lyon (FR); Klaus Kunz, Düsseldorf (DE); Darren Mansfield, Bergisch Gladbach (DE); Amos Mattes, Langenfeld (DE); Oswald Ort, Leverkusen (DE); Philippe Desbordes, Lyons (FR)

(73) Assignee: Bayer Cropscience AG (DE)

( * ) Notice: Subject to any disclaimer, the term of this patent is extended or adjusted under 35 U.S.C. 154(b) by 368 days.

(21) Appl. No.: 12/449,431

(22) PCT Filed: Feb. 21, 2008

(86) PCT No.: PCT/EP2008/052095
§ 371 (c)(1),
(2), (4) Date: Nov. 23, 2009

(87) PCT Pub. No.: WO2008/101976
PCT Pub. Date: Aug. 28, 2008

(65) Prior Publication Data
US 2010/0087494 A1    Apr. 8, 2010

(30) Foreign Application Priority Data
Feb. 22, 2007   (EP) .................................. 07356024

(51) Int. Cl.
*A61K 31/4965* (2006.01)
*C07D 241/10* (2006.01)
(52) U.S. Cl. ........................ 514/249; 544/406
(58) Field of Classification Search ........... 514/249; 544/406
See application file for complete search history.

(56) References Cited

U.S. PATENT DOCUMENTS
4,450,155 A    5/1984   Morgan

FOREIGN PATENT DOCUMENTS

| | | |
|---|---|---|
| CH | 631 158 | 7/1982 |
| EP | 1134214 | 9/2001 |
| JP | 07 112972 | 2/1995 |
| JP | 2006 342116 | 12/2006 |
| WO | WO 00/76979 | 12/2000 |
| WO | WO 01/14339 | 3/2001 |
| WO | WO 03/037274 | 5/2003 |
| WO | WO 2005/066138 | 7/2005 |

OTHER PUBLICATIONS

Ho, B. et al., "Synthesis of 2-piperidinecarboxylic acid derivatives as potential anticonvulsants", *European Journal of Medicinal Chemistry*, vol. 33, 1998, pp. 23-31, XP002438320.

Matecka, D. et al., "Development of Novel, Potent, and Selective Dopamine Reuptake Inhibitors through Alteration of the Piperazine Ring of 1-[2-Diphenylmethoxy)ethyl]- and 1-[2-[Bis(4-fluorophenyl)methoxy]et hy1]-4-(3-phenylpropyl)piperazines (GBR 12935 and GBR 12909)", *Journal of Medicinal Chemistry*, American Chemical Society, vol. 39, No. 24, 1996, pp. 4704-4716, XP002358138, ISSN: 0022-2623.

Wu Y-Q et al., "Solid-Phase Synthesis of FKBP12 Inhibitors: N-Solfonyl and N-Carbamoylprolyl/pipecolyl Amides", *Bioorganic and Medicinal Chemistry Letters*, vol. 12, 2002, pp. 1429-1433, XP002438321.

*Primary Examiner* — Taofiq A Solola
(74) *Attorney, Agent, or Firm* — Ostrolenk Faber LLP

(57) ABSTRACT

A compound of general formula (I):

$$(X)_n\text{-Phenyl-}C(R^1)(R^2)\text{-}C(R^3)(R^4)\text{-}C(R^5)(R^6)\text{-}N(R^7)\text{-}C(=T)\text{-Het}$$
(I)

A process for preparing this compound.
A fungicidal composition comprising a compound of general formula (I).
A method for treating plants by applying a compound of general formula (I) or a composition comprising it.

21 Claims, No Drawings

FUNGICIDE N-(3-PHENYLPROPYL) CARBOXAMIDE DERIVATIVES

CROSS REFERENCE TO RELATED APPLICATION(S)

The present application is a 35 U.S.C. §371 national phase conversion of PCT/EP2008/052095 filed Feb. 21, 2008, which claims priority of European Application No. 07356024.5 filed Feb. 22, 2007.

The present invention relates to fungicide N-(3-phenylpropyl)carboxamide derivatives, their thiocarboxamide or N-substituted carboximidamide analogues, their process of preparation, their use as fungicides, particularly in the form of fungicidal compositions, and methods for the control of phytopathogenic fungi of plants using these compounds or their compositions.

International Patent Application WO 2005/066138 discloses heterocyclic amide derivatives of general formula and their use as fungicides. Compounds according to the present invention are not disclosed in that patent application.

International Patent Application WO 2000/76979 discloses 2-pyridine carboxamide derivatives of general formula encompassing general formula of compounds according to the present invention and their use as fungicides. Compounds according to the present invention are not disclosed in that patent application.

It is always of high-interest in the field of agrochemicals to use pesticidal compounds more active than the compounds already known by the man ordinary skilled in the art whereby less compound can be used whilst retaining equivalent efficacy.

Furthermore, the provision of new pesticidal compounds with a higher efficacy strongly reduces the risk of appearance of resistant strains in the fungi to be treated.

We have now found a new family of compounds which show enhanced fungicidal activity over the general known family of such compounds.

Accordingly, the present invention relates to a N-(3-phenylpropyl)carboxamide derivative of general formula (I)

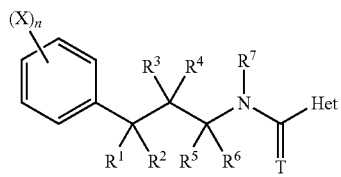

in which:

n is 1, 2, 3, 4 or 5;

T represents O, S, N—$R^a$, N—$OR^b$, N—$NR^aR^b$ or N—CN;

X is a halogen atom, a nitro group, a cyano group, a hydroxy group, an amino group, a sulfanyl group, a pentafluoro-$^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-halogenoalkyl having 1 to 5 halogen atoms a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl or a phenylamino;

$R^1$ and $R^2$ are chosen independently of each other as being a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms or a $C_1$-$C_8$-halogenoalkynyl having 1 to 5 halogen atoms;

$R^3$ and $R^4$ are chosen independently of each other as being a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms or a $C_1$-$C_8$-halogenoalkynyl having 1 to 5 halogen atoms;

$R^5$ and $R^8$ are chosen independently of each other as being a hydrogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms or a $C_1$-$C_8$-halogenoalkynyl having 1 to 5 halogen atoms;

$R^7$ is a hydrogen atom, a $C_1$-$C_8$-alkyl or a $C_3$-$C_7$-cycloalkyl;

$R^a$ and $R^b$, that can be the same or different, represent a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulphonyl; $C_1$-$C_8$-halogenoalkylsulphonyl comprising up to 9 halogen atoms that can be the same or different; phenyl that can be substituted by up to 5 groups Q; naphthyl that can be substituted by up to 6 groups Q; phenylmethylene that can be substituted by up to 5 groups Q; phenylsulphonyl that can be substituted by up to 5 groups Q;

Q, that can be the same or different, represents a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms that can be the same or different; $C_1$-$C_8$-halogenoalkoxy comprising up to 9 halogen atoms that can be the same or different; tri($C_1$-$C_8$)alkylsilyl and tri($C_1$-$C_8$)alkylsilyl-$C_1$-$C_8$-alkyl; $C_1$-$C_8$-alkoxyimino; ($C_1$-$C_8$-alkoxyimino)-$C_1$-$C_8$-alkyl; and Het represents a 5-, 6- or 7-membered non-fused heterocycle with one, two or three heteroatoms which may be the same or different, Het being linked by a carbon atom and Het being substituted in ortho-position by at least one substituent linked by a carbon atom and optionally substituted in any other position by one or further substituents chosen from a halogen atom, a nitro group, a pentafluoro-6-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkyl-sulphonyl, a $C_1$-$C_8$-halogenoalkylsulphonyl having 1 to 5 halogen atoms or a $C_1$-$C_8$-alkylsulfonamide;

as well as its salts, N-oxydes, metallic complexes, metalloidic complexes and optically active isomers;

with the proviso that compound of formula (I) is different from:

4,6-dichloro-2-(methylthio)-N-(3-phenylpropyl)-5-pyrimidinecarboxamide, 4-chloro-2-(methylthio)-6-[(2-phenylethyl)amino]-N-(3-phenylpropyl)-5-pyrimidinecarboxamide, 4-chloro-2-(methylthio)-6-[(2-phenylmethyl)amino]-N-(3-phenylpropyl)-5-pyrimidinecarboxamide, 4-chloro-2-(methylthio)-6-(phenylamino)-N-(3-phenylpropyl)-5-pyrimidinecarboxamide, 4-chloro-2-(methylthio)-6-[(2-phenylpropyl)amino]-N-(3-phenylpropyl)-5-pyrimidinecarboxamide, 5-chloro-1-methyl-N-(3-phenylpropyl)-1H-pyrazole-4-carboxamide, N-[3-(4-acetyl phenyl)propyl]-5-chloro-3-methoxythiophene-2-carboxamide, and 4-(3-{[(5-chloro-3-methoxy-2-thienyl)carbonyl]amino}propyl)benzoic acid.

In the context of the present invention:

halogen means fluorine, bromine, chlorine or iodine.

carboxy means —C(=O)OH;

carbonyl means —C(=O)—;

carbamoyl means —C(=O)NH$_2$;

N-hydroxycarbamoyl means —C(=O)NHOH;

an alkyl group, an alkenyl group, and an alkynyl group as well as moieties containing these terms, can be linear or branched; and heteroatom means sulphur, nitrogen or oxygen.

in the case of an amino group or the amino moiety of any other amino-comprising group, substituted by two substituents that can be the same or different, the two substituents together with the nitrogen atom to which they are linked can form a heterocyclyl group, preferably a 5- to 7-membered heterocyclyl group, that can be substituted or that can include other hetero atoms, for example a morpholino group or piperidinyl group.

Any of the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of general formula (I) wherein X represents a hydroxy, a sulfanyl group or an amino group may be found in its tautomeric form resulting from the shift of the proton of said hydroxy, sulfanyl or amino group. Such tautomeric forms of such compounds are also part of the present invention. More generally speaking, all tautomeric forms of compounds of general formula (I) wherein X represents a hydroxy, a sulfanyl group or an amino group, as well as the tautomeric forms of the compounds which can optionally be used as intermediates in the preparation processes, and which will be defined in the description of these processes, are also part of the present invention.

According to the present invention, the phenyl moiety of compound of general formula (I) may be substituted in any position by $(X)_n$, X and n being as defined above. Preferably, the present invention relates to N-(3-phenylpropyl)carboxamide derivative or its thiocarboxamide, of general formula (I) in which the different characteristics may be chosen alone or in combination as being:

as regards n, n is 1 or 2;

as regards T, T is O or S.

as regards X, X is chosen as being a halogen atom, a (hydroxyimino)-$C_1$-$C_8$-alkyl group, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_1$-$C_8$-halogenoalkoxy having 1 to 5 halogen atoms, a $C_3$-$C_8$-cycloalkyl, a $C_3$-$C_8$-halogenocycloalkyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl or a (benzyloxyimino)-$C_1$-$C_6$-alkyl.

According to the present invention, the carbon atoms of the propylic moiety, of compound of formula (I) are substituted by $R^1$, $R^2$, $R^3$, $R^4$, $R^5$ and $R^6$; $R^1$, $R^2$, $R^3$, $R^4$, $R^5$ and $R^6$ being as defined above. Preferably, the present invention also relates to N-(3-phenylpropyl)carboxamide derivative, its thiocarboxamide, of general formula (I) in which in which the different characteristics may be chosen alone or in combination as being:

as regards $R^1$ and $R^2$, $R^1$ and $R^2$ are respectively chosen independently of each other as being a hydrogen atom or a $C_1$-$C_8$-alkyl;

as regards $R^3$ and $R^4$, $R^3$ and $R^4$ are respectively chosen independently of each other as being a hydrogen atom or a $C_1$-$C_8$-alkyl; and as regards $R^5$ and $R^6$, $R^5$ and $R^6$ are respectively chosen independently of each other as being a hydrogen atom or a $C_1$-$C_8$-alkyl.

According to the present invention, the nitrogen atom of the carboxamide or the thiocarboxamide or the carboximidamide moiety of the compound of formula (I) is substituted by $R^7$, $R^7$ being a hydrogen atom, a $C_1$-$C_8$-alkyl or a $C_3$-$C_7$-cycloalkyl. Preferably, the $C_3$-$C_7$-cycloalkyl is cyclopropyl.

According to the present invention, "Het" of the compound of general formula (I) is a 5-, 6- or 7-membered non-fused heterocycle with one, two or three heteroatoms which may be the same or different, Het being linked by a carbon atom and being substituted at least in ortho position by at least one substituent linked by a carbon atom. Preferably, the present invention also relates to N-methyl carboxamide derivative, its thiocarboxamide or N-substituted carboximidamide analogue, of general formula (I) in which the different characteristics may be chosen alone or in combination as being:

Het is chosen as being 2-furan, 3-furan, 4,5-dihydro-3-furan, 2-thiophene, 3-thiophene, 2-pyrrole, 3-pyrrole, 5-oxazole, 4-oxazole, 5-thiazole, 4-thiazole, 5-pyrazole, 4-pyrazole, 3-pyrazole, 3-isoxazole, 4-isoxazole, 5-isoxazole, 4-isothiazole, 4-1,2,3-triazole, 4-thiadiazole, 5-1,2,3-thiadiazole, 4,5-dihydro-4-pyrazole, 2-pyridine, 3-pyridine, 4-pyridine, 1,4-oxathiine, 3,4-dihydro-5-pyran, 2,3-dihydro-1,4-oxathiine, or 2-pyrazine;

Het is substituted in ortho position by a halogen atom, a $C_1$-$C_8$-alkyl or a $C_1$-$C_8$-halogenoalkyl having 1 to 5 halogen atoms; and Het is substituted in any other position by a hydrogen atom, a halogen atom, a $C_1$-$C_8$-alkyl, an amino group, a $C_1$-$C_8$-alkylamino or a di-$C_1$-$C_8$-alkylamino. More preferably, Het is substituted in any other position by a hydrogen atom or a halogen atom.

According to the present invention, "Het" of the compound of general formula (I) may be a five membered ring heterocycle. Specific examples of compounds of the present invention where Het is a five membered heterocycle include:

* Het represents a heterocycle of the general formula (Het-1)

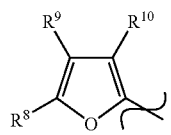
(Het-1)

in which:
$R^8$ and $R^9$ may be the same or different and may be a hydrogen atom, a halogen atom, an amino group, a nitro group, a $C_1$-$C_4$-alkyl or a $C_1$-$C_4$-halogenoalkyl having 1 to 5 halogen atoms; and $R^{10}$ may be a halogen atom, a nitro group, a $C_1$-$C_4$-alkyl or a $C_1$-$C_4$-halogenoalkyl having 1 to 5 halogen atoms.

* Het represents a heterocycle of the general formula (Het-2)

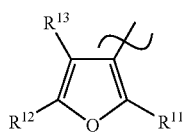
(Het-2)

in which:
$R^{11}$ may be a hydrogen atom, a halogen atom, a $C_1$-$C_4$-alkyl or a $C_1$-$C_4$-halogenoalkyl having 1 to 5 halogen atoms; and $R^{12}$ and $R^{13}$ may be the same or different and may be a hydrogen atom, a halogen atom, an amino group, a $C_1$-$C_4$-alkyl or a $C_1$-$C_4$-halogenoalkyl having 1 to 5 halogen atoms; provided that the $R^{11}$ and $R^{13}$ are not both a hydrogen atom.

* Het represents a heterocycle of the general formula (Het-3)

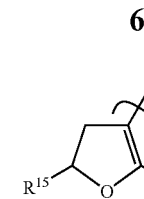
(Het-3)

in which:
$R^{14}$ may be a halogen atom, a $C_1$-$C_4$-alkyl or a $C_1$-$C_4$-halogenoalkyl having 1 to 5 halogen atoms; and $R^{15}$ may be a hydrogen atom, a $C_1$-$C_4$-alkyl or a $C_1$-$C_4$-halogenoalkyl having 1 to 5 halogen atoms.

* Het represents a heterocycle of the general formula (Het-4)

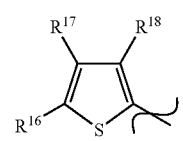
(Het-4)

in which:
$R^{16}$ and $R'^7$ may be the same or different and may be a hydrogen atom, a halogen atom, a $C_1$-$C_4$-alkyl, a $C_1$-$C_4$-halogenoalkyl having 1 to 5 halogen atoms, a $C_1$-$C_4$-alkylthio or a $C_1$-$C_4$-alkylsulphonyl; and $R^{18}$ may be a halogen atom, a cyano group, a $C_1$-$C_4$-alkyl, a $C_1$-$C_4$-halogenoalkyl having 1 to 5 halogen atoms or a $C_1$-$C_4$-halogenoalkoxy having 1 to 5 halogen atoms.

* Het represents a heterocycle of the general formula (Het-5)

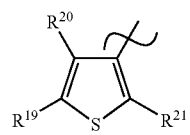
(Het-5)

in which:
$R^{19}$ and $R^{20}$ may be the same or different and may be a hydrogen atom, a halogen atom, a $C_1$-$C_4$-alkyl, a $C_1$-$C_4$-alkyloxy or a $C_1$-$C_4$-halogenoalkyl having 1 to 5 halogen atoms; and $R^{21}$ may be a hydrogen atom, a halogen atom, a $C_1$-$C_4$-alkyl or a $C_1$-$C_4$-halogenoalkyl having 1 to 5 halogen atoms; provided that the $R^{20}$ and $R^{21}$ are not both a hydrogen atom.

* Het represents a heterocycle of the general formula (Het-6)

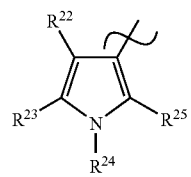
(Het-6)

in which:
$R^{22}$ may be a hydrogen atom, a halogen atom, a cyano group, a $C_1$-$C_4$-alkyl or a $C_1$-$C_4$-halogenoalkyl having 1 to 5 halogen atoms;

$R^{23}$ and $R^{25}$ may be the same or different and may be a hydrogen atom, a halogen atom, a $C_1$-$C_4$-alkyl or a $C_1$-$C_4$-halogenoalkyl having 1 to 5 halogen atoms; and $R^{24}$ may be a hydrogen atom, a cyano group, a $C_1$-$C_4$-alkyl, a $C_1$-$C_4$-halogenoalkyl having 1 to 5 halogen atoms, a $C_1$-$C_4$-alkoxy-$C_1$-$C_4$-alkyl, a hydroxy-$C_1$-$C_4$-alkyl, a $C_1$-$C_4$-alkylsulphonyl, a di($C_1$-$C_4$-alkyl)aminosulphonyl or a $C_1$-$C_6$-alkylcarbonyl;

provided that the $R^{22}$ and $R^{25}$ are not both a hydrogen atom.

* Het represents a heterocycle of the general formula (Het-7)

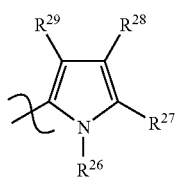

(Het-7)

in which:

$R^{26}$ may be a hydrogen atom, a cyano group, a $C_1$-$C_4$-alkyl, a $C_1$-$C_4$-halogenoalkyl having 1 to 5 halogen atoms, a $C_1$-$C_4$-alkoxy-$C_1$-$C_4$-alkyl, a hydroxy-$C_1$-$C_4$-alkyl, a $C_1$-$C_4$-alkylsulphonyl, a di($C_1$-$C_4$-alkyl)aminosulphonyl or a $C_1$-$C_6$-alkylcarbonyl; and $R^{27}$ and $R^{28}$ may be the same or different and may be a hydrogen atom, a halogen atom, a cyano group, a $C_1$-$C_4$-alkyl, a $C_1$-$C_4$-halogenoalkyl having 1 to 5 halogen atoms or a $C_1$-$C_4$-alkylcarbonyl;

$R^{29}$ may be a halogen atom, a cyano group, a $C_1$-$C_4$-alkyl, a $C_1$-$C_4$-halogenoalkyl having 1 to 5 halogen atoms or a $C_1$-$C_4$-alkylcarbonyl;

* Het represents a heterocycle of the general formula (Het-8)

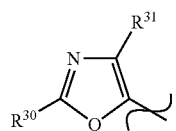

(Het-8)

in which:

$R^{30}$ may be a hydrogen atom or a $C_1$-$C_4$-alkyl; and $R^{31}$ may be a halogen atom, a $C_1$-$C_4$-alkyl or a $C_1$-$C_4$-halogenoalkyl having 1 to 5 halogen atoms.

* Het represents a heterocycle of the general formula (Het-9)

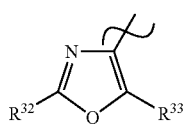

(Het-9)

in which:

$R^{32}$ may be a hydrogen atom or a $C_1$-$C_4$-alkyl; and $R^{33}$ may be a halogen atom, a $C_1$-$C_4$-alkyl, a $C_1$-$C_4$-halogenoalkyl having 1 to 5 halogen atoms or a phenyl optionally substituted by a halogen atom or a $C_1$-$C_4$-alkyl.

* Het represents a heterocycle of the general formula (Het-10)

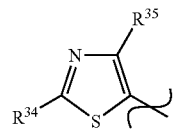

(Het-10)

in which:

$R^{34}$ may be a hydrogen atom, a halogen atom, an amino group, a cyano group, a $C_1$-$C_4$-alkylamino, a di-($C_1$-$C_4$-alkyl)amino, a $C_1$-$C_4$-alkyl or a $C_1$-$C_4$-halogenoalkyl having 1 to 5 halogen atoms; and $R^{35}$ may be a halogen atom, a $C_1$-$C_4$-alkyl or a $C_1$-$C_4$-halogenoalkyl having 1 to 5 halogen atoms.

* Het represents a heterocycle of the general formula (Het-11)

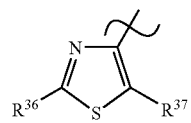

(Het-11)

in which:

$R^{36}$ may be a hydrogen atom, a halogen atom, an amino group, a cyano group, a $C_1$-$C_4$-alkylamino, a di-($C_1$-$C_4$-alkyl)amino, a $C_1$-$C_4$-alkyl or a $C_1$-$C_4$-halogenoalkyl having 1 to 5 halogen atoms; and $R^{37}$ may be a halogen atom, a $C_1$-$C_4$-alkyl or a $C_1$-$C_4$-halogenoalkyl having 1 to 5 halogen atoms.

* Het represents a heterocycle of the general formula (Het-12)

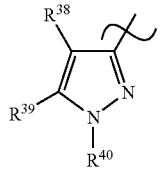

(Het-12)

in which:

$R^{38}$ may be a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl group or an aminocarbonyl-$C_1$-$C_4$-alkyl;

$R^{39}$ may be a hydrogen atom, a halogen atom, a cyano group, a nitro group, a $C_1$-$C_4$-alkyl, a $C_1$-$C_4$-alkoxy or a $C_1$-$C_4$-alkylthio; and $R^{40}$ may be a hydrogen atom, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl or a $C_1$-$C_4$-halogenoalkoxy-$C_1$-$C_4$-alkyl having 1 to 5 halogen atoms.

* Het represents a heterocycle of the general formula (Het-13)

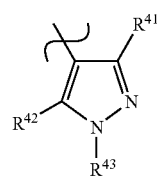
(Het-13)

in which:

$R^{41}$ may be a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl or an aminocarbonyl-$C_1$-$C_4$-alkyl;

$R^{42}$ may be a hydrogen atom, a halogen atom, a cyano group, a $C_1$-$C_4$-alkyl, a $C_1$-$C_4$-alkoxy, a $C_1$-$C_4$-halogenoalkoxy having 1 to 5 halogen atoms or a $C_1$-$C_4$-alkylthio; and $R^{43}$ may be a hydrogen atom, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, a $C_1$-$C_4$-halogenoalkoxy-$C_1$-$C_4$-alkyl having 1 to 5 halogen atoms or a phenyl optionally substituted by a halogen atom, a $C_1$-$C_4$-alkyl, a $C_1$-$C_4$-alkoxyalkyl or a nitro group;

provided that the $R^{41}$ and $R^{42}$ are not both a hydrogen atom.

* Het represents a heterocycle of the general formula (Het-14)

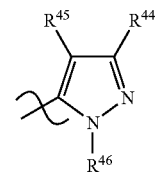
(Het-14)

in which:

$R^{44}$ may be a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl, or an aminocarbonyl-$C_1$-$C_4$-alkyl;

$R^{45}$ may a halogen atom, a cyano group, a $C_1$-$C_4$-alkyl, a $C_1$-$C_4$-alkoxy, a $C_1$-$C_4$-alkylthio or a $C_1$-$C_4$-halogenoalky having 1 to 5 halogen atoms;

$R^{46}$ may be a hydrogen atom, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, a $C_1$-$C_4$-halogenoalkoxy-$C_1$-$C_4$-alkyl having 1 to 5 halogen atoms;

* Het represents a heterocycle of the general formula (Het-15)

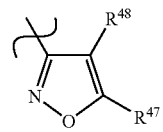
(Het-15)

in which:

$R^{47}$ may be a hydrogen atom, a halogen atom, a $C_1$-$C_4$-alkyl or a $C_1$-$C_4$-halogenoalkyl having 1 to 5 halogen atoms; and $R^{48}$ may be a halogen atom, a $C_1$-$C_4$-alkyl or a $C_1$-$C_4$-halogenoalkyl having 1 to 5 halogen atoms.

* Het represents a heterocycle of the general formula (Het-16)

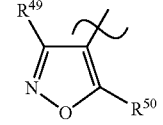
(Het-16)

in which $R^{49}$ and $R^{50}$ may be the same or different and may be a hydrogen atom, a halogen atom, a $C_1$-$C_4$-alkyl or a $C_1$-$C_4$-halogenoalkyl having 1 to 5 halogen atoms;

provided that $R^{49}$ and $R^{50}$ are not both a hydrogen atom.

* Het represents a heterocycle of the general formula (Het-17)

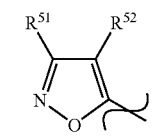
(Het-17)

in which $R^{51}$ may be a halogen atom, a $C_1$-$C_4$-alkyl or a $C_1$-$C_4$-halogenoalkyl having 1 to 5 halogen atoms, and $R^{52}$ may be a halogen atom, a $C_1$-$C_4$-alkyl or a $C_1$-$C_4$-halogenoalkyl having 1 to 5 halogen atoms.

* Het represents a heterocycle of the general formula (Het-18)

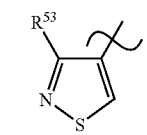
(Het-18)

in which $R^{53}$ may be a halogen atom, a $C_1$-$C_4$-alkyl or a $C_1$-$C_4$-halogenoalkyl having 1 to 5 halogen atoms.

* Het represents a heterocycle of the general formula (Het-19)

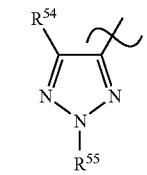
(Het-19)

in which:

$R^{54}$ may be a halogen atom, a $C_1$-$C_4$-alkyl or a $C_1$-$C_4$-halogenoalkyl having 1 to 5 halogen atoms; and $R^{55}$ may be a hydrogen atom, a $C_1$-$C_4$-alkyl or a $C_1$-$C_4$-halogenoalkyl having 1 to 5 halogen atoms.

* Het represents a heterocycle of the general formula (Het-20)

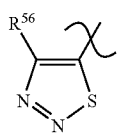
(Het-20)

in which $R^{56}$ may be a halogen atom, a $C_1$-$C_4$-alkyl or a $C_1$-$C_4$-halogenoalkyl having 1 to 5 halogen atoms.

* Het represents a heterocycle of the general formula (Het-21)

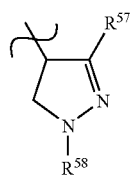
(Het-21)

in which:

$R^{57}$ may be a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl or an aminocarbonyl-$C_1$-$C_4$-alkyl; and $R^{58}$ may be a hydrogen atom, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, a $C_1$-$C_4$-halogenoalkoxy-$C_1$-$C_4$-alkyl having 1 to 5 halogen atoms or a phenyl optionally substituted by a halogen atom, a $C_1$-$C_4$-alkyl, a $C_1$-$C_4$-alkoxyalkyl or a nitro group;

According to the present invention, "Het" of the compound of general formula (I) may be a six membered ring heterocycle. Specific examples of compounds of the present invention where Het is a six membered heterocycle include:

* Het represents a heterocycle of the general formula (Het-22)

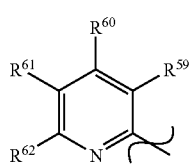
(Het-22)

in which:

$R^{59}$ may be a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms or a $C_1$-$C_4$-halogenoalkoxy having 1 to 5 halogen atoms; and $R^{60}$, $R^{61}$ and $R^{62}$, which may be the same or different, may be a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl or a $C_1$-$C_4$-alkylsulphonyl.

* Het represents a heterocycle of the general formula (Het-23)

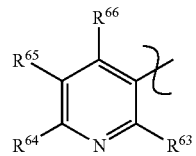
(Het-23)

in which:

$R^{63}$ may be a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_5$-alkylthio, a $C_2$-$C_5$-alkenylthio a $C_1$-$C_4$-halogenoalkylthio having 1 to 5 halogen atoms or a $C_1$-$C_4$-halogenoalkoxy having 1 to 5 halogen atoms;

$R^{64}$, $R^{65}$ and $R^{66}$, which may the same or different, may be a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl or a $C_1$-$C_4$-alkylsulphonyl;

provided that the $R^{63}$ and $R^{66}$ are not both a hydrogen atom.

* Het represents a heterocycle of the general formula (Het-24)

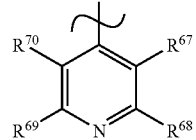
(Het-24)

in which:

$R^{67}$, $R^{68}$, $R^{69}$ and $R^{70}$, which may be the same or different, may be a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms, a $C_1$-$C_4$-halogenoalkoxy having 1 to 5 halogen atoms, a $C_1$-$C_4$-alkylsulphinyl or a $C_1$-$C_4$-alkylsulphonyl;

provided that the $R^{67}$ and $R^{70}$ are not both a hydrogen atom.

* Het represents a heterocycle of the general formula (Het-25)

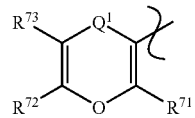
(Het-25)

in which:

$Q^1$ may be a sulphur atom, —SO— or —SO$_2$—;

$R^{71}$ may be a $C_1$-$C_4$-alkyl or a $C_1$-$C_4$-halogenoalkyl having 1 to 5 halogen atoms; and $R^{72}$ and $R^{73}$ may be the same or different and may be a hydrogen atom or a $C_1$-$C_4$-alkyl.

* Het represents a heterocycle of the general formula (Het-26)

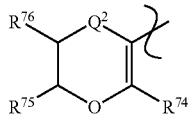
(Het-26)

in which:

Q$^1$ may be a sulphur atom, —SO—, —SO$_2$— or —CH$_2$—;

R$^{74}$ may be a C$_1$-C$_4$-alkyl or a C$_1$-C$_4$-halogenoalkyl having 1 to 5 halogen atoms; and R$^{75}$ and R$^{76}$ may be the same or different and may be a hydrogen atom or a C$_1$-C$_4$-alkyl.

* Het represents a heterocycle of the general formula (Het-27)

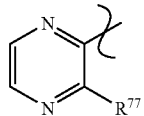
(Het-27)

in which R$^{77}$ may be a halogen atom, a C$_1$-C$_4$-alkyl or a C$_1$-C$_4$-halogenoalkyl having 1 to 5 halogen atoms.

The present invention also relates to a process for the preparation of the compound of general formula (I). Thus, according to a further aspect of the present invention there is provided a process P1 for the preparation of compound of general formula (I) wherein T represents O, as defined above, which comprises reacting a 3-phenylpropan-1-amine derivative of general formula (II) or one of its salt:

Process P1

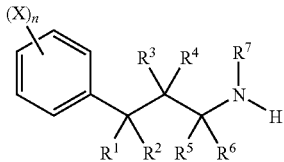
(II)

in which X, n, R$^1$, R$^2$, R$^3$, R$^4$, R$^5$, R$^6$ and R$^7$ are as defined above; with a carboxylic acid derivative of the general formula (III)

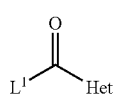
(III)

in which:

* Het is as defined above; and

L$^1$ is a leaving group chosen as being a halogen atom, a hydroxyl group, —OR$^c$, —OCOR$^c$, R$^c$ being a C$_1$-C$_6$ alkyl, a C$_1$-C$_6$ haloalkyl, a benzyl, 4-methoxybenzyl, pentafluorophenyl or a

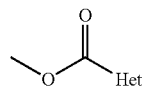

in the presence of a catalyst and, if L$^1$ is a hydroxyl group, in the presence of a condensing agent.

The process according to the present invention is conducted in the presence of a catalyst. Suitable catalyst may be chosen as being 4-dimethyl-aminopyridine, 1-hydroxy-benzotriazole or dimethylformamide.

In case L$^1$ is a hydroxy group, the process according to the present invention is conducted in the presence of condensing agent. Suitable condensing agent may be chosen as being acid halide former, such as phosgene, phosphorous tribromide, phosphorous trichloride, phosphorous-pentachloride, phosphorous trichloride oxide or thionyl chloride; anhydride former, such as ethyl chloroformate, methyl chloroformate, isopropyl chloroformate, isobutyl chloroformate or methanesulfonyl-chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromotripyrrolidino-phosphonium-hexafluorophosphate.

When R$^7$ is a hydrogen atom, the above mentioned process for the preparation of compound of general formula (I) wherein T represents O, may optionally be completed by a further step according to the following reaction scheme (process P2):

Process P2

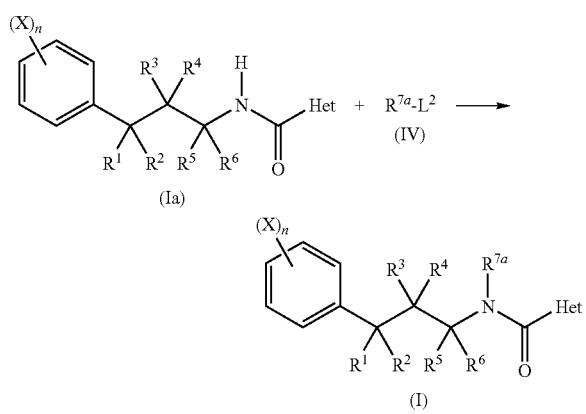

in which:

R$^1$, R$^2$, R$^3$, R$^4$, R$^5$, R$^6$, Het, X, and n are as defined above;

R$^{72}$ is a hydrogen atom, a C$_1$-C$_6$-alkyl or a C$_3$-C$_7$-cycloalkyl; and L$^2$ is a leaving group chosen as being a halogen atom, a 4-methyl phenylsulfonyloxy or a methylsulfonyloxy;

comprising the reaction of a compound of general formula (Ia) with a compound of general formula (IV) to provide a compound of general formula (I).

According to a further aspect according to the invention, there is provided a process P3 for the preparation of a compound of formula (I), wherein T represents S, and illustrated according to the following reaction scheme:

Process P3

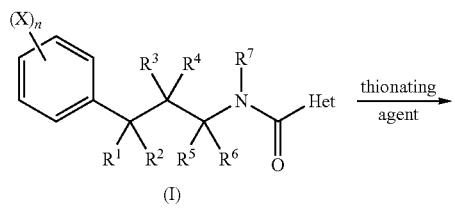

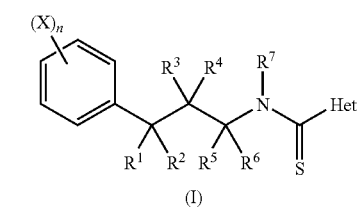

in which X, n, R¹, R², R³, R⁴, R⁵, R⁶, R⁷ and Het are as defined above;

Process P3 can be performed in the presence of a thionating agent.

Starting amide derivatives of formula (I) can be prepared according to processes P1 or P2. Suitable thionating agents for carrying out process P3 according to the invention can be sulphur (S), sulfhydric acid ($H_2S$), sodium sulfide ($Na_2S$), sodium hydrosulfide (NaHS), boron trisulfide ($B_2S_3$), bis(diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in *J. Chem. Soc. Perkin* 1, (2001), 358.

in the presence or in the absence, of a catalytic or stoechiometric or more, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylaminopyridine or N-methylpiperidine.

According to a further aspect according to the invention, there is provided a process P4 for the preparation of compound of formula (I), wherein T represents N—$R^a$, N—$OR^b$, N—$NR^aR^b$ or N—CN, and illustrated according to the following reaction scheme:

Process P4

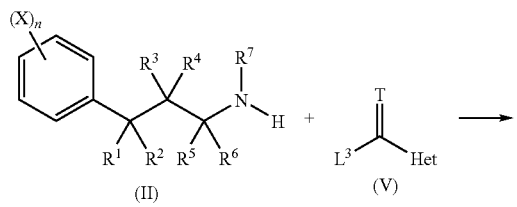

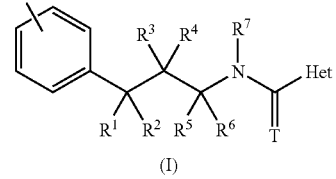

in which:

R¹, R², R³, R⁴, R⁵, R⁶, R⁷, Het, X, and n are as defined above;

$L^3$ being a chlorine atom;

comprising the reaction of a compound of general formula (II) with a compound of general formula (V) to provide a compound of general formula (I).

N-substituted carboximidoyl chloride of formula (V) are known or can be prepared by known processes, for example as described in Houben-Weyl, "Methoden der organischen Chemie" (1985), E5/1, 628-633 and Patai, "The chemistry of amidines and imidates" (1975), 296-301.

Suitable acid binders for carrying out process P4 according to the invention can be inorganic and organic bases that are customary for such reactions. Preference is given to using alkaline earth metal or alkali metal hydroxides, such as sodium hydroxide, calcium hydroxide, potassium hydroxide or other ammonium hydroxide derivatives; alkali metal carbonates, such as sodium carbonate, potassium carbonate, potassium bicarbonate, sodium bicarbonate; alkali metal or alkaline earth metal acetates, such as sodium acetate, potassium acetate, calcium acetate; alkaline earth metal or alkali metal hydrides, such as sodium hydride or potassium hydride; alkaline earth metal or alkali metal alcoolates, such as sodium methylate, sodium ethylate, sodium propylate or potassium t-butylate; and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU); or a polymer-supported acid scavenger (for example as detailed in http://www.iris-biotech.de/downloads/scavengers.pdf). It is also possible to work in the absence of any additional acid binder.

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesise.

On the basis of his general knowledge and of available publications, the skilled worker will also be able to prepare intermediate compound of formula (II) according to the present invention.

The present invention also relates to a fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Optionally, additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds of the invention can also be mixed with one or more insecticides, fungicides, bactericides, attractant acaricides or pheromones or other compounds with biological activity. The mixtures thus obtained have a broadened spectrum of activity. The mixtures with other fungicides are particularly advantageous. Examples of suitable fungicide mixing partners may be selected in the following lists:

1) a compound capable to inhibit the nucleic acid synthesis like benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid;

2) a compound capable to inhibit the mitosis and cell division like benomyl, carbendazim, diethofencarb, ethaboxam, fuberidazole, pencycuron, thiabendazole thiophanate-methyl, zoxamide;

3) a compound capable to inhibit the respiration for example
as CI-respiration inhibitor like diflumetorim;
as CII-respiration inhibitor like boscalid, carboxin, fenfuram, flutolanil, furametpyr, furmecyclox, mepronil, oxycarboxine, penthiopyrad, thifluzamide; isopyrazam
as CIII-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

4) a compound capable of to act as an uncoupler like dinocap, fluazinam, meptyldinocap;

5) a compound capable to inhibit ATP production like fentin acetate, fentin chloride, fentin hydroxide, silthiofam;

6) a compound capable to inhibit AA and protein biosynthesis like andoprim, blasticidin-S, cyprodinil, kasugamycin, kasugamycin hydrochloride hydrate, mepanipyrim, pyrimethanil;

7) a compound capable to inhibit the signal transduction like fenpiclonil, fludioxonil, quinoxyfen;

8) a compound capable to inhibit lipid and membrane synthesis like biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl, vinclozolin;

9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, fusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

10) a compound capable to inhibit cell wall synthesis like benthiavalicarb, bialaphos, dimethomorph, flumorph, iprovalicarb, mandipropamid, polyoxins, polyoxorim, validamycin A;

11) a compound capable to inhibit melanine biosynthesis like carpropamid, diclocymet, fenoxanil, phthalide, pyroquilon, tricyclazole;

12) a compound capable to induce a host defence like acibenzolar-S-methyl, probenazole, tiadinil;

13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxinecopper, propineb, sulphur and sulphur preparations including calcium polysulphide, thiram, tolylfluanid, zineb, ziram;

14) a compound selected in the following list: (2E)-2-(2-{[6-(3-chloro-2-methylphenoxy)-5-fluoropyrimidin-4-yl]oxy}phenyl)-2-(methoxyimino)-N-methylacetamide, (2E)-

2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylate, 2,3,5,6-tetrachloro-4-(methylsulfonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts, 3,4,5-trichloropyridine-2,6-dicarbonitrile, 3,4-dichloro-N-(2-cyanophenyl)isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo[1,5-a]pyrimidin-7-amine, 5-chloro-7-(4-methylpiperidin-1-yl)-6-(2,4,6-trifluorophenyl)[1,2,4]triazolo[1,5-a]pyrimidine, 5-chloro-N-[(1R)-1,2-dimethylpropyl]-6-(2,4,6-trifluorophenyl)[1, 2, 4]triazolo[1, 5-a]pyrimidin-7-amine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fluthianil, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl isothiocyanate, metrafenone, mildiomycin, N-[2-(1,3-dimethylbutyl)phenyl]-5-fluoro-1,3-dimethyl-1H-pyrazole-4-carboxamide, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(4-{[3-(4-chlorophenyl)prop-2-yn-1-yl]oxy}-3-methoxyphenyl)ethyl]-N<-(methylsulfonyl)valinamide, N-{(Z)-[(cyclopropylmethoxy)imino][6-(difluoromethoxy)-2,3-difluorophenyl]methyl}-2-phenylacetamide, N-{2-[1,1'-bi(cyclopropyl)-2-yl]phenyl}-3-(difluoromethyl)-, 1-methyl-1H-pyrazole-4-carboxamide, N-{2-[3-chloro-5-(trifluoromethyl)pyridin-2-yl]ethyl}-2-(trifluoromethyl)benzamide, natamycin, N-ethyl-N-methyl-N'-{2-methyl-5-(trifluoromethyl)-4-[3-(trimethylsilyl)propoxy]phenyl}imidoformamide, N-ethyl-N-methyl-N'-{2-methyl-5-(difluoromethyl)-4-[3-(trimethylsilyl)propoxy]phenyl}imidoformamide, nickel dimethyldithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyribencarb, pyrrolnitrine, quintozene, tecloftalam, tecnazene, triazoxide, trichlamide, valiphenal, zarilamid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The fungicidal compositions of the present invention can be used to curatively or preventively control the phytopathogenic fungi of crops. Thus, according to a further aspect of the present invention, there is provided a method for curatively or preventively controlling the phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the present invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases of plants or crops that can be controlled by the method according to the present invention, mention may be made of:

Powdery mildew diseases such as:

*Blumeria* diseases, caused for example by *Blumeria graminis*;

*Podosphaera* diseases, caused for example by *Podosphaera leucotricha*;

*Sphaerotheca* diseases, caused for example by *Sphaerotheca fuliginea*;

*Uncinula* diseases, caused for example by *Uncinula necator*;

Rust diseases such as:

*Gymnosporangium* diseases, caused for example by *Gymnosporangium sabinae*;

*Hemileia* diseases, caused for example by *Hemileia vastatrix*;

*Phakopsora* diseases, caused for example by *Phakopsora pachyrhizi* or *Phakopsora meibomiae*;

*Puccinia* diseases, caused for example by *Puccinia recondite*;

*Uromyces* diseases, caused for example by *Uromyces appendiculatus*;

Oomycete diseases such as:

*Bremia* diseases, caused for example by *Bremia lactucae*;

*Peronospora* diseases, caused for example by *Peronospora pisi* or *P. brassicae*;

*Phytophthora* diseases, caused for example by *Phytophthora infestans*;

*Plasmopara* diseases, caused for example by *Plasmopara viticola*;

*Pseudoperonospora* diseases, caused for example by *Pseudoperonospora humuli* or *Pseudoperonospora cubensis*;

*Pythium* diseases, caused for example by *Pythium ultimum*;

Leafspot, leaf blotch and leaf blight diseases such as:

*Alternaria* diseases, caused for example by *Alternaria solani*;

*Cercospora* diseases, caused for example by *Cercospora beticola*;

*Cladiosporum* diseases, caused for example by *Cladiosporium cucumerinum*;

*Cochliobolus* diseases, caused for example by *Cochliobolus sativus*;

*Colletotrichum* diseases, caused for example by *Colletotrichum lindemuthanium*;

*Cycloconium* diseases, caused for example by *Cycloconium oleaginum*;

*Diaporthe* diseases, caused for example by *Diaporthe citri*;

*Elsinoe* diseases, caused for example by *Elsinoe fawcettii*;

*Gloeosporium* diseases, caused for example by *Gloeosporium laeticolor*;

*Glomerella* diseases, caused for example by *Glomerella cingulata*;

*Guignardia* diseases, caused for example by *Guignardia bidwelli*;

*Leptosphaeria* diseases, caused for example by *Leptosphaeria maculans*; *Leptosphaeria nodorum*;

*Magnaporthe* diseases, caused for example by *Magnaporthe grisea*;

*Mycosphaerella* diseases, caused for example by *Mycosphaerella graminicola*; *Mycosphaerella arachidicola*; *Mycosphaerella fijiensis*;

*Phaeosphaeria* diseases, caused for example by *Phaeosphaeria nodorum*;

*Pyrenophora* diseases, caused for example by *Pyrenophora teres*;

*Ramularia* diseases, caused for example by *Ramularia collo-cygni*;

*Rhynchosporium* diseases, caused for example by *Rhynchosporium secalis*;

*Septoria* diseases, caused for example by *Septoria apii* or *Septoria lycopercisi*;

*Typhula* diseases, caused for example by *Typhula incarnate*;

*Venturia* diseases, caused for example by *Venturia inaequalis*;

Root and stem diseases such as:

*Corticium* diseases, caused for example by *Corticium graminearum*;

*Fusarium* diseases, caused for example by *Fusarium oxysporum*;

*Gaeumannomyces* diseases, caused for example by *Gaeumannomyces graminis*;

*Rhizoctonia* diseases, caused for example by *Rhizoctonia solani*;

*Tapesia* diseases, caused for example by *Tapesia acuformis*;

*Thielaviopsis* diseases, caused for example by *Thielaviopsis basicola*;

Ear and panicle diseases such as:

*Alternaria* diseases, caused for example by *Alternaria* spp.;

*Aspergillus* diseases, caused for example by *Aspergillus flavus*;

*Cladosporium* diseases, caused for example by *Cladosporium* spp.;

*Claviceps* diseases, caused for example by *Claviceps purpurea*;

*Fusarium* diseases, caused for example by *Fusarium culmorum*;

*Gibberella* diseases, caused for example by *Gibberella zeae*;

*Monographella* diseases, caused for example by *Monographella nivalis*;

Smut and bunt diseases such as:

*Sphacelotheca* diseases, caused for example by *Sphacelotheca reiliana*;

*Tilletia* diseases, caused for example by *Tilletia caries*;

*Urocystis* diseases, caused for example by *Urocystis occulta*;

*Ustilago* diseases, caused for example by *Ustilago nuda*;

Fruit rot and mould diseases such as:

*Aspergillus* diseases, caused for example by *Aspergillus flavus*;

*Botrytis* diseases, caused for example by *Botrytis cinerea*;

*Penicillium* diseases, caused for example by *Penicillium expansum*;

*Sclerotinia* diseases, caused for example by *Sclerotinia sclerotiorum*;

*Verticilium* diseases, caused for example by *Verticilium alboatrum*;

Seed and soilborne decay, mould, wilt, rot and damping-off diseases:

*Fusarium* diseases, caused for example by *Fusarium culmorum*;

*Phytophthora* diseases, caused for example by *Phytophthora cactorum*;

*Pythium* diseases, caused for example by *Pythium ultimum*;

*Rhizoctonia* diseases, caused for example by *Rhizoctonia solani*;

*Sclerotium* diseases, caused for example by *Sclerotium rolfsii*;

*Microdochium* diseases, caused for example by *Microdochium nivale*;

Canker, broom and dieback diseases such as:

*Nectria* diseases, caused for example by *Nectria galligena*;

Blight diseases such as:

*Monilinia* diseases, caused for example by *Monilinia taxa*;

Leaf blister or leaf curl diseases such as:

*Taphrina* diseases, caused for example by *Taphrina deformans;*

Decline diseases of wooden plants such as:

*Esca* diseases, caused for example by *Phaemoniella clamydospora;*

Diseases of flowers and Seeds such as:

*Botrytis* diseases, caused for example by *Botrytis cinerea;*

Diseases of tubers such as:

*Rhizoctonia* diseases, caused for example by *Rhizoctonia solani;*

*Helminthosporium* diseases, caused for example by *Helminthosporium*

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. The dose of active substance applied is generally and advantageously between 2 and 200 g per 100 kg of seed, preferably between 3 and 150 g per 100 kg of seed in the case of seed treatment.

It is clearly understood that the doses indicated above are given as illustrative examples of the invention. A person skilled in the art will know how to adapt the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used for the preparation of composition useful to curatively or preventively treat human and animal fungal diseases such as, for example, mycoses, dermatoses, trichophyton diseases and candidiases or diseases caused by *Aspergillus* spp., for example *Aspergillus fumigatus*.

The aspects of the present invention will now be illustrated with reference to the following tables of compounds and examples. The following Table illustrates in a non-limiting manner examples of fungicidal compounds according to the present invention. In the following Examples, M+1 (or M−1) means the molecular ion peak, plus or minus 1 a.m.u. (atomic mass units) respectively, as observed in mass spectroscopy and M (Apcl+) means the molecular ion peak as it was found via positive atmospheric pressure chemical ionisation in mass spectroscopy.

TABLE A

| Compound | $R^1$ | $R^2$ | $R^3$ | $R^4$ | $R^5$ | $R^6$ | $R^7$ | $X^1$ | $X^2$ | $X^3$ | $X^4$ | $X^5$ | T | $Y^1$ | $Y^2$ | $Y^a$ | (M + 1) |
|---|---|---|---|---|---|---|---|---|---|---|---|---|---|---|---|---|---|
| A-1 | H | H | H | H | H | H | H | Cl | H | Cl | H | H | O | H | H | $CF_3$ | 382 |
| A-2 | H | H | H | H | H | H | H | Cl | H | Cl | H | H | O | H | H | I | 440 |
| A-3 | H | H | H | H | H | H | H | Cl | H | Cl | H | H | O | H | H | Me | 328 |

TABLE B

| Compound | $R^1$ | $R^2$ | $R^3$ | $R^4$ | $R^5$ | $R^6$ | $R^7$ | $X^1$ | $X^2$ | $X^3$ | $X^4$ | $X^5$ | T | $Y^1$ | $Y^2$ | Q | $Y^a$ | (M + 1) |
|---|---|---|---|---|---|---|---|---|---|---|---|---|---|---|---|---|---|---|
| B-1 | H | H | H | H | H | H | H | Cl | H | Cl | H | H | O | H | H | S | $CF_3$ | 400 |

TABLE C

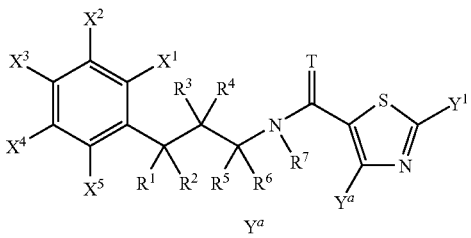

| Compound | R¹ | R² | R³ | R⁴ | R⁵ | R⁶ | R⁷ | X¹ | X² | X³ | X⁴ | X⁵ | T | Y¹ | Yᵃ | (M + 1) |
|---|---|---|---|---|---|---|---|---|---|---|---|---|---|---|---|---|
| C-1 | H | H | H | H | H | H | H | Cl | H | Cl | H | H | O | Me | CHF₂ | 379 |

TABLE D

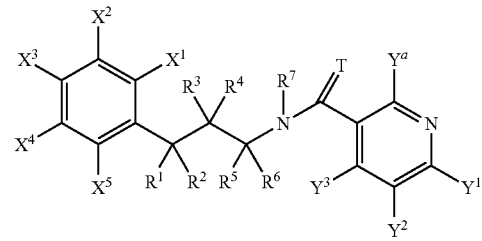

| Compound | R¹ | R² | R³ | R⁴ | R⁵ | R⁶ | R⁷ | X¹ | X² | X³ | X⁴ | X⁵ | T | Y¹ | Y² | Y³ | Yᵃ | (M + 1) |
|---|---|---|---|---|---|---|---|---|---|---|---|---|---|---|---|---|---|---|
| D-1 | H | H | H | H | H | H | H | Cl | H | Cl | H | H | O | H | H | H | Cl | 343 |

TABLE E

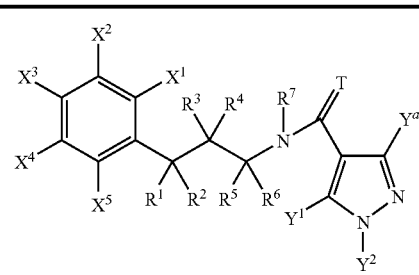

| Compound | R¹ | R² | R³ | R⁴ | R⁵ | R⁶ | R⁷ | X¹ | X² | X³ | X⁴ | X⁵ | T | Y¹ | Y² | Yᵃ | (M + 1) |
|---|---|---|---|---|---|---|---|---|---|---|---|---|---|---|---|---|---|
| E-1 | H | H | H | H | H | H | H | Cl | H | Cl | H | H | O | F | Me | Me | 344 |
| E-2 | H | H | H | H | H | H | H | Cl | H | Cl | H | H | O | F | Me | CF₃ | 398 |
| E-3 | H | H | H | H | H | H | H | Cl | H | Cl | H | H | O | H | Me | Et | 340 |
| E-4 | H | H | H | H | H | H | H | Cl | H | Cl | H | H | O | H | Me | EtO | 356 |
| E-5 | H | H | H | H | H | H | H | Cl | H | Cl | H | H | O | H | Me | CF₃ | 380 |
| E-6 | H | H | H | H | H | H | H | Cl | H | Cl | H | H | O | H | Me | CHF₂ | 362 |
| E-7 | H | H | H | H | H | H | H | Cl | H | Cl | H | H | O | H | Me | MeO | 342 |
| E-8 | H | H | H | H | H | H | H | Cl | H | Cl | H | H | O | H | Me | I | 438 |
| E-9 | H | H | H | H | H | H | H | Cl | H | Cl | H | H | O | Cl | Me | Me | 360 |
| E-10 | H | H | H | H | H | Me | cPr | Cl | H | Cl | H | H | O | F | Me | Me | 398 |
| E-11 | Me | H | H | H | H | H | cPr | H | H | H | H | H | O | F | Me | Me | 330 |
| E-12 | H | H | H | H | H | Me | cPr | CF3 | H | H | H | H | O | F | Me | Me | 398 |
| E-13 | H | H | H | H | H | Me | cPr | H | Cl | H | H | H | O | F | Me | Me | 398 |
| E-14 | H | H | H | H | H | Me | cPr | H | Cl | Cl | H | H | S | F | Me | Me | 414 |

TABLE F

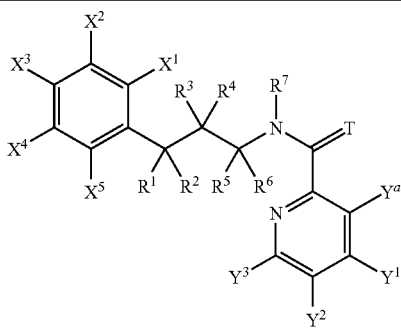

| Compound | R$^1$ | R$^2$ | R$^3$ | R$^4$ | R$^5$ | R$^6$ | R$^7$ | X$^1$ | X$^2$ | X$^3$ | X$^4$ | X$^5$ | T | Y$^1$ | Y$^2$ | Y$^3$ | Y$^a$ | (M + 1) |
|---|---|---|---|---|---|---|---|---|---|---|---|---|---|---|---|---|---|---|
| F-1 | H | H | H | H | H | H | H | Cl | H | Cl | H | H | O | H | H | H | CF$_3$ | 377 |

TABLE G

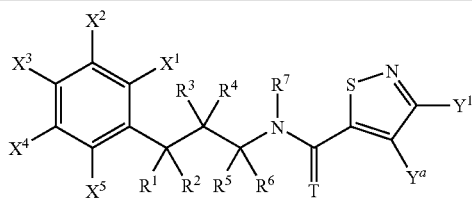

| Compound | R$^1$ | R$^2$ | R$^3$ | R$^4$ | R$^5$ | R$^6$ | R$^7$ | X$^1$ | X$^2$ | X$^3$ | X$^4$ | X$^5$ | T | Y$^1$ | Y$^2$ | (M + 1) |
|---|---|---|---|---|---|---|---|---|---|---|---|---|---|---|---|---|
| G-1 | H | H | H | H | H | H | H | Cl | H | Cl | H | H | O | Cl | Cl | 383 |

TABLE H

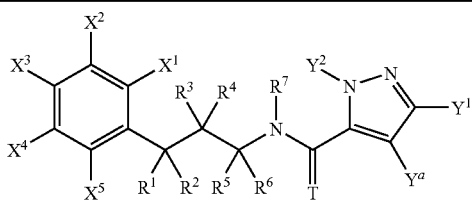

| Compound | R$^1$ | R$^2$ | R$^3$ | R$^4$ | R$^5$ | R$^6$ | R$^7$ | X$^1$ | X$^2$ | X$^3$ | X$^4$ | X$^5$ | T | Y$^1$ | Y$^2$ | Y$^a$ | (M + 1) |
|---|---|---|---|---|---|---|---|---|---|---|---|---|---|---|---|---|---|
| H-1 | H | H | H | H | H | H | H | Cl | H | Cl | H | H | O | Me | Et | Br | 419 |

EXAMPLES OF PROCESS FOR THE PREPARATION OF THE COMPOUND OF GENERAL FORMULA (I)

Preparation of N-[3-(2,4-dichlorophenyl)propyl]-3-iodothiophene-2-carboxamide (compound A-2)

3-iodothiophene-2-carboxylic acid (411 mg, 1.617 mmol), DMF (0.002 ml, 0.026 mmol) and thionyl chloride (2 mml, 27.42 mmol) are stirred at 80° C. for two hours. The reaction mixture was concentrated in vacuo and the crude product was diluted in dichloromethane (2 ml), added to a mixture of 3-(2,4-dichlorophenyl)propan-1-amine (3000 mg, 1.47 mmol) and triethylamine (246 µl, 1.34 mmol) in dichloromethane (5 ml). The reaction mixture was stirred for 48 hours at room temperature.

The reaction mixture was filtered through a plug of basic alumina.

The filtrate was concentrated in vacuo, purified by flash chromatography on silica (ethyl acetate/heptane) to yield to N-[3-(2,4-dichlorophenyl)propyl]-3-iodothiophene-2-carboxamide: 314 mg (42%).

Mass spectrum: 440 (M+1).

General Preparation: Thionation of an Amide Derivative of Formula (I) on Chemspeed™ Apparatus In a 13 ml Chemspeed™ vial is weighted 0.27 mmole of phosphorous pentasulfide (P$_2$S$_5$). 3 ml of a 0.18 molar solution of the amide (1) (0.54 mmole) in dioxane is added and the mixture is heated at reflux for two hours. The temperature is then cooled to 80° C. and 2.5 ml of water are added. The mixture is heated at 80° C. for one more hour. 2 ml of water are then added and the reaction mixture is extracted twice by 4 ml of dichloromethane. The organic phase is deposited on a basic alumina cardridge (2 g) and eluted twice by 8 ml of dichloromethane. The solvents are removed and the crude thioamide is analyzed by LCMS and NMR. Insufficiently pure compounds are further purified by preparative LCMS.

Examples of Biological Activity of the Compound of General Formula (I)

Example A

In Vivo Test on *Sphaerotheca fuliginea* (Powdery Mildew)

The active ingredients tested are prepared by homogenization in a mixture of acetone/tween/water. This suspension is then diluted with water to obtain the desired active material concentration.

Gherkin plants (Vert petit de Paris variety) in starter cups, sown on a 50/50 peat soil-pozzolana substrate and grown at 20° C./23° C., are treated at the cotyledon Z11 stage by spraying with the aqueous suspension described above. Plants, used as controls, are treated with an aqueous solution not containing the active material.

After 24 hours, the plants are contaminated by spraying them with an aqueous suspension of *Sphaerotheca fuliginea* spores (100 000 spores per ml). The spores are collected from a contaminated plants. The contaminated gerkhin plants are incubated at about 20° C./25° C. and at 60/70% relative humidity.

Grading (% of efficacy) is carried out 21 days after the contamination, in comparison with the control plants.

Under these conditions, good (at least 70%) or total protection is observed at a dose of 500 ppm with the following compounds: A2, C1, E2, E5, E6, E8 and F1.

Example B

In Vivo Test on *Pyrenophora teres* (Barley Net Blotch)

The active ingredients tested are prepared by homogenization in a mixture of acetone/tween/DMSO, then diluted with water to obtain the desired active material concentration.

Barley plants (Express variety), sown on a 50/50 peat soil-pozzolana substrate in starter cups and grown at 12° C., are treated at the 1-leaf stage (10 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants.

Under these conditions, good (at least 70%) or total protection is observed at a dose of 500 ppm with the following compounds: B1, C1, E5, E6, E8, E9 and F1.

Example C

In Vivo Test on *Alternaria brassicae* (Leaf Spot of Crucifers)

The active ingredients tested are prepared by potter homogenisation in a mixture of acetone/tween/water. This suspension is then diluted with water to obtain the desired active material concentration.

Radish plants (Pernot variety), sown on a 50/50 peat soil-pozzolana substrate in starter cups and grown at 18-20° C., are treated at the cotyledon stage by spraying with the active ingredient prepared as described above.

Plants, used as controls, are treated with the mixture of acetone/tween/water not containing the active material.

After 24 hours, the plants are contaminated by spraying them with an aqueous suspension of *Alternaria brassicae* spores (40,000 spores per cm$^3$). The spores are collected from a 12 to 13 days-old culture.

The contaminated radish plants are incubated for 6-7 days at about 18° C., under a humid atmosphere.

Grading is carried out 6 to 7 days after the contamination, in comparison with the control plants.

Under these conditions, good protection (at least 70%) is observed at a dose of 500 ppm with the following compounds: C1, D1, E1, E5, E6 and E9.

Example D

Cell Test on *Mycosphaerella graminicola*

The growth of *Mycosphaerella graminicola* is performed in a bactopeptone based liquid medium at 20° C. under shaking (120 rpm) during 72 hours. The bactopeptone based medium is prepared by mixing 14.6 grams of D-glucose, 1.4 grams of Yeast extract and 7.1 g of bacteriological peptone (OXOID ref. LP0037) in 1 liter of demineralized water. The medium is sterilized by autoclave 15 minutes at 121° C. After 72 hours, pre-culture of *Mycosphaerella graminicola* is recovered and the optic density (OD) at 620 nm is adjusted with the bactopeptone based medium at 0.5. The compounds are dissolved in DMSO and added to sterile liquid bactopeptone medium at a concentration of 6 ppm. The medium is inoculated with the pre-culture of *Mycosphaerella graminicola* by a dilution of 10 times of the pre-culture. The efficacy of the compounds is assessed by OD measurement at 620 nm after 4 days at 20° C. in comparison with a control.

Under these conditions, the following compounds showed good (at least 70%) protection at the dose of 6 ppm.: A1, A2, B1, C1, D1, E1, E2, E5, E6, and F1.

Under similar conditions, N-(3,3-diphenylpropyl)-3-hydroxy-4-methoxypyridine-2-carboxamide (i.e. compound 16 disclosed in International Patent Application WO 00/76979) and (3-(4-chlorophenyl)-N-[3-(3,4-dimethoxyphenyl)propyl]-5-methylisoxazole-4-carboxamide) (i.e. compound 60 disclosed in International Patent Application WO 2005/066138) did not show any activity.

The invention claimed is:
1. A compound of formula (I)

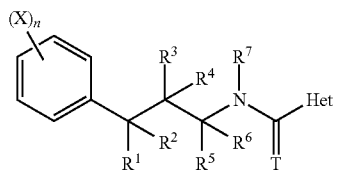

wherein:
n is 1, 2, 3, 4 or 5;
T is selected from the group consisting of O, S, N—$R^a$, N—$OR^b$, N—$NR^aR^b$ and N—CN;
each X is independently selected from the group consisting of a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_3$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl-$C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl and a phenylamino;
$R^1$ and $R^2$ are independently selected from the group consisting of a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;
$R^3$ and $R^4$ are independently selected from the group consisting of a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms or and a $C_1$-$C_8$-halogenoalkynyl having 1 to 5 halogen atoms;
$R^5$ and $R^6$ are independently selected from the group consisting of a hydrogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;
$R^7$ is selected from the group consisting of a hydrogen atom, a $C_1$-$C_6$-alkyl and a $C_3$-$C_7$-cycloalkyl;
$R^a$ and $R^b$ are independently selected from the group consisting of a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulfonyl; $C_1$-$C_8$-halogenoalkylsulfonyl comprising up to 9 halogen atoms that can be the same or different; phenyl that can be substituted by up to 5 groups Q; naphthyl that can be substituted by up to 6 groups Q; phenylmethylene that can be substituted by up to 5 groups Q; and phenylsulfonyl that can be substituted by up to 5 groups Q;
each Q is independently selected from the group consisting of a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms that can be the same or different; $C_1$-$C_8$-halogenoalkoxy comprising up to 9 halogen atoms that can be the same or different; tri($C_1$-$C_8$)alkylsilyl and tri($C_1$-$C_8$)alkylsilyl-$C_1$-$C_8$-alkyl; $C_1$-$C_8$-alkoxyimino; and ($C_1$-$C_8$-alkoxyimino)-$C_1$-$C_8$-alkyl; and
Het is a 5-, 6- or 7-membered non-fused heterocycle with one, two or three heteroatoms which may be the same or different, Het being linked by a carbon atom and Het being substituted in ortho-position by at least one substituent linked by a carbon atom and optionally substituted in any other position by one or further more substituents independently selected from the group consisting of a halogen atom, a nitro group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms and a $C_1$-$C_8$-alkylsulfonamide;

as well as any salt, N-oxide, metallic complex, metalloidic complex, or optically active isomer thereof;

with the proviso that compound of formula (I) is different from:

4,6-dichloro-2-(methylthio)-N-(3-phenylpropyl)-5-pyrimidinecarboxamide, 4-chloro-2-(methylthio)-6-[(2-phenylethyl)amino]-N-(3-phenylpropyl)-5-pyrimidinecarboxamide, 4-chloro-2-(methylthio)-6-[(2-phenylmethyl)amino]-N-(3-phenylpropyl)-5-pyrimidinecarboxamide, 4-chloro-2-(methylthio)-6-(phenylamino)-N-(3-phenylpropyl)-5-pyrimidinecarboxamide, 4-chloro-2-(methylthio)-6-[(2-phenylpropyl)amino]-N-(3-phenylpropyl)-5-pyrimidinecarboxamide, 5-chloro-1-methyl-N-(3-phenylpropyl)-1H-pyrazole-4-carboxamide, N-[3-(4-acetylphenyl)propyl]-5-chloro-3-methoxythiophene-2-carboxamide, and 4-(3-{[(5-chloro-3-methoxy-2-thienyl)carbonyl]amino}propyl)benzoic acid.

2. The compound of claim 1 wherein n is 1 or 2.

3. The compound of claim 1 wherein each X is independently selected from the group consisting of a halogen atom, a (hydroxyimino)-$C_1$-$C_6$-alkyl group, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_1$-$C_8$-halogenoalkoxy having 1 to 5 halogen atoms, a $C_3$-$C_8$-cycloalkyl, a $C_3$-$C_8$-halogenocycloalkyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl and a (benzyloxyimino)-$C_1$-$C_6$-alkyl.

4. The compound of claim 1 wherein $R^1$ and $R^2$ are independently selected from the group consisting of a hydrogen atom and a $C_1$-$C_8$-alkyl.

5. The compound of claim 1 wherein $R^3$ and $R^4$ are independently selected from the group consisting of a hydrogen atom and a $C_1$-$C_8$-alkyl.

6. The compound of claim 1 wherein $R^5$ and $R^6$ are independently selected from the group consisting of a hydrogen atom and a $C_1$-$C_8$-alkyl.

7. The compound of claim 1 wherein Het is selected from the group consisting of 2-furan, 3-furan, 4,5-dihydro-3-furan, 2-thiophene, 3-thiophene, 2-pyrrole, 3-pyrrole, 5-oxazole, 4-oxazole, 5-thiazole, 4-thiazole, 5-pyrazole, 4-pyrazole, 3-pyrazole, 4-isoxazole, 5-isoxazole, 4-isothiazole, 4-1,2,3-triazole, 4-thiadiazole, 5-1,2,3-thiadiazole, 4,5-dihydro-4-pyrazole, 2-pyridine, 3-pyridine, 4-pyridine, 1,4-oxathiine, 3,4-dihydro-5-pyran, 2,3-dihydro-1,4-oxathiine, and 2-pyrazine.

8. The compound of claim 1 wherein Het is substituted in ortho position by a moiety selected from the group consisting of a halogen atom, a $C_1$-$C_8$-alkyl and a $C_1$-$C_8$-halogenoalkyl having 1 to 5 halogen atoms.

9. The compound of claim 1 wherein Het is substituted in any position different from the ortho position by a moiety selected from the group consisting of a halogen atom, a $C_1$-$C_6$-alkyl, an amino group, a $C_1$-$C_8$-alkylamino and a di-$C_1$-$C_8$-alkylamino.

10. The compound of claim 1 wherein Het is a 5-membered heterocycle.

11. The compound of claim 1 wherein $R^7$ is hydrogen.

12. The compound of claim 1 wherein T is oxygen.

13. A process for the preparation of the compound of claim 1 comprising reacting a 3-phenylpropan-1-amine derivative of formula (II) or a salt thereof:

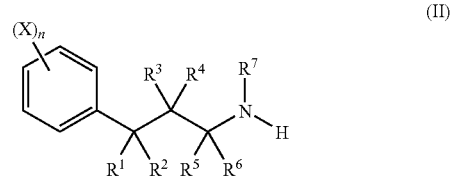

wherein:
n is 1, 2, 3, 4 or 5;
each X is independently selected from the group consisting of a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-halogenoalkyl having 1 to 5 halogen atoms a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_3$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl and a phenylamino;

$R^1$ and $R^2$ are independently selected from the group consisting of a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

$R^3$ and $R^4$ are independently selected from the group consisting of a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$- cycloalkyl, a $C_3$-$C_8$-halogenocycloalkyl having 1 to 5 halogen atoms, a $C_1$-$C_8$-halogenoalkenyl having 1 to 5 halogen atoms or and a $C_1$-$C_8$-halogenoalkynyl having 1 to 5 halogen atoms;

$R^5$ and $R^6$ are independently selected from the group consisting of a hydrogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms; and $R^7$ is selected from the group consisting of a hydrogen atom, a $C_1$-$C_6$-alkyl and a $C_3$-$C_7$-cycloalkyl;

with a carboxylic acid derivative of the formula (III)

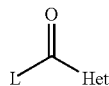
(III)

wherein:

Het is a 5-, 6- or 7-membered non-fused heterocycle with one, two or three heteroatoms which may be the same or different, Het being linked by a carbon atom and Het being substituted in ortho-position by at least one substituent linked by a carbon atom and optionally substituted in any other position by one or more substituents independently selected from the group consisting of a halogen atom, a nitro group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms and a $C_1$-$C_8$-alkylsulfonamide; and L is a leaving group selected from the group consisting of a halogen atom, a hydroxyl group, —$OR^a$, —$OCOR^a$, $R^a$ being a $C_1$-$C_6$-alkyl, a $C_1$-$C_6$ haloalkyl, a benzyl, 4-methoxybenzyl, pentafluorophenyl or a group of formula

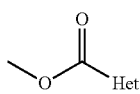

in the presence of a catalyst and, if L is a hydroxyl group, in the presence of a condensing agent.

14. The process of claim 13 wherein $R^7$ is a hydrogen atom, said process further comprising the step:

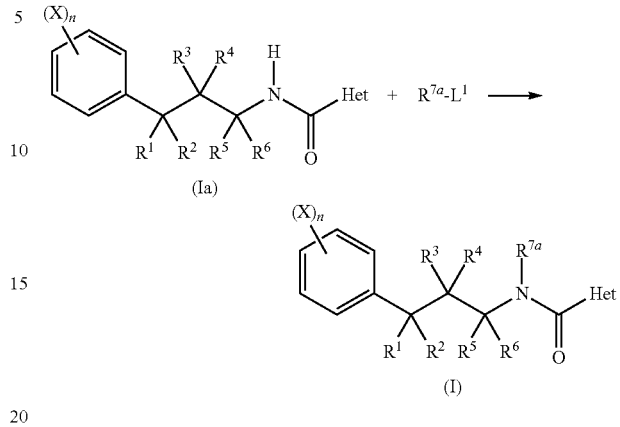

wherein:

$R^1$ and $R^2$ are independently selected from the group consisting of a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

$R^3$ and $R^4$ are independently selected from the group consisting of a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms or and a $C_1$-$C_8$-halogenoalkynyl having 1 to 5 halogen atoms;

$R^5$ and $R^6$ are independently selected from the group consisting of a hydrogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

Het is a 5-, 6- or 7-membered non-fused heterocycle with one, two or three heteroatoms which may be the same or different, Het being linked by a carbon atom and Het being substituted in ortho-position by at least one substituent linked by a carbon atom and optionally substituted in any other position by one or more substituents independently selected from the group consisting of a halogen atom, a nitro group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a C$_1$-C$_8$-alkylsulfonyl, a C$_1$-C$_8$-halogenoalkylsulfonyl having 1 to 5 halogen atoms and a C$_1$-C$_8$-alkylsulfonamide;

each X is independently selected from the group consisting of a halogen atom, a nitro group, a cyano group, a hydroxy group, an amino group, a sulfanyl group, a pentafluoro-λ$^6$-sulfanyl group, a formyl group, a formyloxy group, a formylamino group, a carboxy group, a carbamoyl group, a N-hydroxycarbamoyl group, a carbamate group, a (hydroxyimino)-C$_1$-C$_6$-alkyl group, a C$_1$-C$_8$-halogenoalkyl having 1 to 5 halogen atoms a C$_1$-C$_8$-alkyl, a C$_2$-C$_3$-alkenyl, a C$_2$-C$_8$-alkynyl, a C$_1$-C$_8$-alkylamino, a di-C$_1$-C$_8$-alkylamino, a C$_1$-C$_8$-alkoxy, a C$_1$-C$_8$-halogenoalkoxy having 1 to 5 halogen atoms, a C$_1$-C$_8$-alkylsulfanyl, a C$_1$-C$_8$-halogenoalkylsulfanyl having 1 to 5 halogen atoms, a C$_2$-C$_8$-alkenyloxy, a C$_2$-C$_8$-halogenoalkenyloxy having 1 to 5 halogen atoms, a C$_3$-C$_8$-alkynyloxy, a C$_3$-C$_8$-halogenoalkynyloxy having 1 to 5 halogen atoms, a C$_3$-C$_8$-cycloalkyl, a C$_3$-C$_8$-halogenocycloalkyl having 1 to 5 halogen atoms, a C$_1$-C$_8$-alkylcarbonyl, a C$_1$-C$_8$-halogenoalkylcarbonyl having 1 to 5 halogen atoms, a C$_1$-C$_8$-alkylcarbamoyl, a di-C$_1$-C$_8$-alkylcarbamoyl, a N—C$_1$-C$_8$-alkyloxycarbamoyl, a C$_1$-C$_8$-alkoxycarbamoyl, a N—C$_1$-C$_8$-alkyl-C$_1$-C$_8$-alkoxycarbamoyl, a C$_1$-C$_8$-alkoxycarbonyl, a C$_1$-C$_8$-halogenoalkoxycarbonyl having 1 to 5 halogen atoms, a C$_1$-C$_8$-alkylcarbonyloxy, a C$_1$-C$_8$-halogenoalkylcarbonyloxy having 1 to 5 halogen atoms, a C$_1$-C$_8$-alkylcarbonylamino, a C$_1$-C$_8$-halogenoalkylcarbonylamino having 1 to 5 halogen atoms, a C$_1$-C$_8$-alkylaminocarbonyloxy, a di-C$_1$-C$_8$-alkylaminocarbonyloxy, a C$_1$-C$_8$-alkyloxycarbonyloxy, a C$_1$-C$_8$-alkylsulfenyl, a C$_1$-C$_8$-halogenoalkylsulfenyl having 1 to 5 halogen atoms, a C$_1$-C$_8$-alkylsulfinyl, a C$_1$-C$_8$-halogenoalkylsulfinyl having 1 to 5 halogen atoms, a C$_1$-C$_8$-alkylsulfonyl, a C$_1$-C$_8$-halogenoalkylsulfonyl having 1 to 5 halogen atoms, a C$_1$-C$_6$-alkoxyimino, a (C$_1$-C$_6$-alkoxyimino)-C$_1$-C$_6$-alkyl, a (C$_1$-C$_6$-alkenyloxyimino)-C$_1$-C$_6$-alkyl, a (C$_1$-C$_6$-alkynyloxyimino)-C$_1$-C$_6$-alkyl, a (benzyloxyimino)-C$_1$-C$_6$-alkyl, a benzyloxy, a benzylsulfanyl, a benzylamino, a phenoxy, a phenylsulfanyl and a phenylamino;

n is 1, 2, 3, 4 or 5;

R$^{7a}$ is selected from the group consisting of a hydrogen atom, a C$_1$-C$_6$-alkyl and a C$_3$-C$_7$-cycloalkyl; and L$^1$ is a leaving group selected from the group consisting of a halogen atom, a 4-methyl phenylsulfonyloxy and a methylsulfonyloxy;

comprising reacting a compound of formula (Ia) with a compound of formula (III) to provide the compound of formula (I).

15. A fungicide composition comprising an effective amount of the compound of claim 1 and an agriculturally acceptable support.

16. A method for combating the phytopathogenic fungi of crops comprising applying an effective and non-phytotoxic amount of the composition of claim 15 to the plant seeds or to the plant leaves and/or to the fruits of the plants or to the soil in which the plants are growing or in which it is desired to grow them.

17. A method for combating the phytopathogenic fungi of crops comprising applying an effective and non-phytotoxic amount of the compound of claim 1 to the plant seeds or to the plant leaves or to the fruits of the plants or to the soil in which the plants are growing or in which it is desired to grow them.

18. A compound of formula (I)

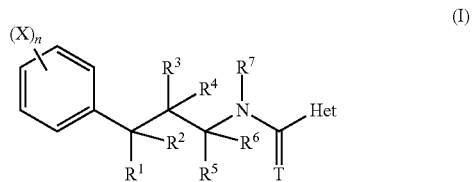

wherein:

n is 1, 2, 3, 4 or 5;

T is selected from the group consisting of O, S, N—R$^a$, N—OR$^b$, N—NR$^a$R$^b$ and N—CN;

each X is independently selected from the group consisting of a halogen atom, a nitro group, a cyano group, a hydroxy group, an amino group, a sulfanyl group, a pentafluoro-λ$^6$-sulfanyl group, a formyl group, a formyloxy group, a formylamino group, a carboxy group, a carbamoyl group, a N-hydroxycarbamoyl group, a carbamate group, a (hydroxyimino)-C$_1$-C$_6$-alkyl group, a C$_1$-C$_8$-halogenoalkyl having 1 to 5 halogen atoms, a C$_1$-C$_8$-alkyl, a C$_2$-C$_8$-alkenyl, a C$_2$-C$_8$-alkynyl, a C$_1$-C$_8$-alkylamino, a di-C$_1$-C$_8$-alkylamino, a C$_1$-C$_3$-alkoxy, a C$_1$-C$_8$-halogenoalkoxy having 1 to 5 halogen atoms, a C$_1$-C$_8$-alkylsulfanyl, a C$_1$-C$_8$-halogenoalkylsulfanyl having 1 to 5 halogen atoms, a C$_2$-C$_8$-alkenyloxy, a C$_2$-C$_8$-halogenoalkenyloxy having 1 to 5 halogen atoms, a C$_3$-C$_8$-alkynyloxy, a C$_3$-C$_8$-halogenoalkynyloxy having 1 to 5 halogen atoms, a C$_3$-C$_8$-cycloalkyl, a C$_3$-C$_8$-halogenocycloalkyl having 1 to 5 halogen atoms, a C$_1$-C$_8$-alkylcarbonyl, a C$_1$-C$_8$-halogenoalkylcarbonyl having 1 to 5 halogen atoms, a C$_1$-C$_8$-alkylcarbamoyl, a di-C$_1$-C$_8$-alkylcarbamoyl, a N—C$_1$-C$_8$-alkyloxycarbamoyl, a C$_1$-C$_8$-alkoxycarbamoyl, a N—C$_1$-C$_8$-alkyl-C$_1$-C$_8$-alkoxycarbamoyl, a C$_1$-C$_8$-alkoxycarbonyl, a C$_1$-C$_8$-halogenoalkoxycarbonyl having 1 to 5 halogen atoms, a C$_1$-C$_8$-alkylcarbonyloxy, a C$_1$-C$_8$-halogenoalkylcarbonyloxy having 1 to 5 halogen atoms, a C$_1$-C$_8$-alkylcarbonylamino, a C$_1$-C$_8$-halogenoalkylcarbonylamino having 1 to 5 halogen atoms, a C$_1$-C$_8$-alkylaminocarbonyloxy, a di-C$_1$-C$_8$-alkylaminocarbonyloxy, a C$_1$-C$_8$-alkyloxycarbonyloxy, a C$_1$-C$_8$-alkylsulfenyl, a C$_1$-C$_8$-halogenoalkylsulfenyl having 1 to 5 halogen atoms, a C$_1$-C$_8$-alkylsulfinyl, a C$_1$-C$_8$-halogenoalkylsulfinyl having 1 to 5 halogen atoms, a C$_1$-C$_8$-alkylsulfonyl, a C$_1$-C$_8$-halogenoalkylsulfonyl having 1 to 5 halogen atoms, a C$_1$-C$_6$-alkoxyimino, a (C$_1$-C$_6$-alkoxyimino)-C$_1$-C$_6$-alkyl, a (C$_1$-C$_6$-alkenyloxyimino)-C$_1$-C$_6$-alkyl, a (C$_1$-C$_6$-alkynyloxyimino)-C$_1$-C$_6$-alkyl, a (benzyloxyimino)-C$_1$-C$_6$-alkyl, a benzyloxy, a benzylsulfanyl, a benzylamino, a phenoxy, a phenylsulfanyl and a phenylamino;

R$^1$ and R$^2$ are independently selected from the group consisting of a hydrogen atom, a halogen atom, a C$_1$-C$_8$-halogenoalkyl having 1 to 5 halogen atoms, a C$_1$-C$_8$-alkyl, a C$_2$-C$_8$-alkenyl, a C$_2$-C$_8$-alkynyl, a C$_3$-C$_8$-cycloalkyl, a C$_3$-C$_8$-halogenocycloalkyl having 1 to 5 halogen atoms, a C$_1$-C$_8$-halogenoalkenyl having 1 to 5 halogen atoms and a C$_1$-C$_8$-halogenoalkynyl having 1 to 5 halogen atoms;

R$^3$ and R$^4$ are independently selected from the group consisting of a hydrogen atom, a halogen atom, a C$_1$-C$_8$-halogenoalkyl having 1 to 5 halogen atoms, a C$_1$-C$_8$-alkyl, a C$_2$-C$_8$-alkenyl, a C$_2$-C$_8$-alkynyl, a C$_3$-C$_8$- cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

$R^5$ and $R^6$ independently selected from the group consisting of a hydrogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

$R^7$ is selected from the group consisting of a hydrogen atom, a $C_1$-$C_6$-alkyl and a $C_3$-$C_7$-cycloalkyl;

$R^a$ and $R^b$ are independently selected from the group consisting of a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulfonyl; $C_1$-$C_8$-halogenoalkylsulfonyl comprising up to 9 halogen atoms that can be the same or different; phenyl that can be substituted by up to 5 groups Q; naphthyl that can be substituted by up to 6 groups Q; phenylmethylene that can be substituted by up to 5 groups Q; and phenylsulfonyl that can be substituted by up to 5 groups Q;

each Q is independently selected from the group consisting of a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms that can be same or different; $C_1$-$C_8$-halogenoalkoxy comprising up to 9 halogen atoms that can be the same or different; tri($C_1$-$C_8$)alkylsilyl and tri($C_1$-$C_8$)alkylsilyl-$C_1$-$C_8$-alkyl; $C_1$-$C_8$-alkoxyimino; and ($C_1$-$C_8$-alkoxyimino)-$C_1$-$C_8$-alkyl; and Het is a 6-membered non-fused heterocycle with one, two or three heteroatoms which may be the same or different, Het being linked by a carbon atom and Het being substituted in ortho-position by at least one substituent linked by a carbon atom and optionally substituted in any other position by one or more substituents independently selected from the group consisting of a halogen atom, a nitro group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms and a $C_1$-$C_8$-alkylsulfonamide;

as well as any salt, N-oxide, metallic complek, metalloidic complex, or optically active isomer thereof;

with the proviso that compound of formula (I) is different from:

4,6-dichloro-2-(methylthio)-N-(3-phenylpropyl)-5-pyrimidinecarboxamide, 4-chloro-2-(methylthio)-6-[(2-phenylethyl)amino]-N-(3-phenylpropyl)-5-pyrimidinecarboxamide, 4-chloro-2-(methylthio)-6-[(2-phenylmethyl)amino]-N-(3-phenylpropyl)-5-pyrimidinecarboxamide, 4-chloro-2-(methylthio)-6-(phenylamino)-N-(3-phenylpropyl)-5-pyrimidinecarboxamide, 4-chloro-2-(methylthio)-6-[(2-phenylpropyl)amino]-N-(3-phenylpropyl)-5-pyrimidinecarboxamide, 5-chloro-1-methyl-N-(3-phenylpropyl)-1H-pyrazole-4-carboxamide, N-[3-(4-acetylphenyl)propyl]-5-chloro-3-methoxythiophene-2-carboxamide, and 4-(3-{[(5-chloro-3-methoxy-2-thienyl)carbonyl]amino}propyl)benzoic acid.

19. A compound of formula (I)

$$(I)$$

wherein:

n is 1, 2, 3, 4 or 5;

T is selected from the group consisting of O, S, N—$R^a$, N—$OR^b$, N—$NR^aR^b$ and N—CN;

each X is independently selected from the group consisting of a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_3$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl and a phenylamino;

$R^1$ and $R^2$ are independently selected from the group consisting of a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

$R^3$ and $R^4$ are independently selected from the group consisting of a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

$R^5$ and $R^6$ independently selected from the group consisting of a hydrogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

$R^7$ is cyclopropyl;

$R^a$ and $R^b$ are independently selected from the group consisting of a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_2$-cycloalkyl; $C_3$-$C_2$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulfonyl; $C_1$-$C_8$-halogenoalkylsulfonyl comprising up to 9 halogen atoms that can be the same or different; phenyl that can be substituted by up to 5 groups Q; naphthyl that can be substituted by up to 6 groups Q; phenylmethylene that can be substituted by up to 5 groups Q; and phenylsulfonyl that can be substituted by up to 5 groups Q;

each Q is independently selected from the group consisting of a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms that can be the same or different; $C_1$-$C_8$-halogenoalkoxy comprising up to 9 halogen atoms that can be the same or different; tri($C_1$-$C_8$)alkylsilyl and tri($C_1$-$C_8$)alkylsilyl-$C_1$-$C_8$-alkyl; $C_1$-$C_8$-alkoxyimino; and ($C_1$-$C_8$-alkoxyimino)-$C_1$-$C_8$-alkyl; and Het is a 5-, 6- or 7-membered non-fused heterocycle with one, two or three heteroatoms which may be the same or different, Het being linked by a carbon atom and Het being substituted in ortho-position by at least one substituent linked by a carbon atom and optionally substituted in any other position by one or more substituents independently selected from the group consisting of a halogen atom, a nitro group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms and a $C_1$-$C_8$-alkylsulfonamide;

as well as any salt, N-oxide, metallic complex, metalloidic complex, or optically active isomer thereof;

with the proviso that compound of formula (I) is different from:

4,6-dichloro-2-(methylthio)-N-(3-phenylpropyl)-5-pyrimidinecarboxamide, 4-chloro-2-(methylthio)-6-[(2-phenylethyl)amino]-N-(3-phenylpropyl)-5-pyrimidinecarboxamide, 4-chloro-2-(methylthio)-6-[(2-phenylmethyl)amino]-N-(3-phenylpropyl)-5-pyrimidinecarboxamide, 4-chloro-2-(methylthio)-6-(phenylamino)-N-(3-phenylpropyl)-5-pyrimidinecarboxamide, 4-chloro-2-(methylthio)-6-[(2-phenylpropyl)amino]-N-(3-phenylpropyl)-5-pyrimidinecarboxamide, 5-chloro-1-methyl-N-(3-phenylpropyl)-1H-pyrazole-4-carboxamide, N-[3-(4-acetylphenyl)propyl]-5-chloro-3-methoxythiophene-2-carboxamide, and 4-(3-{[(5-chloro-3-methoxy-2-thienyl)carbonyl]amino}propyl)benzoic acid.

20. A compound of formula (I)

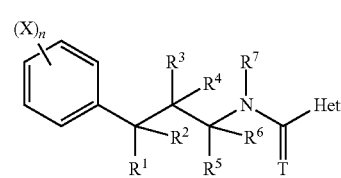

wherein:

n is 1, 2, 3, 4 or 5;

T is sulfur;

each X is independently selected from the group consisting of a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_3$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl and a phenylamino;

$R^1$ and $R^2$ are independently selected from the group consisting of a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

$R^3$ and $R^4$ are independently selected from the group consisting of a hydrogen atom, a halogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

$R^5$ and $R^6$ independently selected from the group consisting of a hydrogen atom, a $C_1$-$C_8$-halogenoalkyl having 1 to 5 halogen atoms, a $C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-halogenoalkenyl having 1 to 5 halogen atoms and a $C_1$-$C_8$-halogenoalkynyl having 1 to 5 halogen atoms;

$R^7$ is selected from the group consisting of a hydrogen atom, a $C_1$-$C_6$-alkyl and a $C_3$-$C_7$-cycloalkyl; and Het is a 5-, 6- or 7-membered non-fused heterocycle with one, two or three heteroatoms which may be the same or different, Het being linked by a carbon atom and Het being substituted in ortho-position by at least one substituent linked by a carbon atom and optionally substituted in any other position by one or more substituents independently selected from the group consisting of a halogen atom, a nitro group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms and a $C_1$-$C_8$-alkylsulfonamide;

as well as any salt, N-oxide, metallic complex, metalloidic complex, or optically active isomer thereof;

with the proviso that compound of formula (I) is different from:

4,6-dichloro-2-(methylthio)-N-(3-phenylpropyl)-5-pyrimidinecarboxamide, 4-chloro-2-(methylthio)-6-[(2-phenylethyl)amino]-N-(3-phenylpropyl)-5-pyrimidinecarboxamide, 4-chloro-2-(methylthio)-6-[(2-phenylmethyl)amino]-N-(3-phenylpropyl)-5-pyrimidinecarboxamide, 4-chloro-2-(methylthio)-6-(phenylamino)-N-(3-phenylpropyl)-5-pyrimidinecarboxamide, 4-chloro-2-(methylthio)-6-[(2-phenylpropyl)amino]-N-(3-phenylpropyl)-5-pyrimidinecarboxamide, 5-chloro-1-methyl-N-(3-phenylpropyl)-1H-pyrazole-4-carboxamide, N-[3-(4-acetylphenyl)propyl]-5-chloro-3-methoxythiophene-2-carboxamide, and 4-(3-{[(5-chloro-3-methoxy-2-thienyl)carbonyl]amino}propyl)benzoic acid.

21. The compound of claim 1 wherein Het is selected from the group consisting of 2-furan, 3-furan, 4,5-dihydro-3-furan, 2-thiophene, 3-thiophene, 2-pyrrole, 3-pyrrole, 5-oxazole, 4-oxazole, 5-thiazole, 4-thiazole, 5-pyrazole, 4-pyrazole, 3-pyrazole, 3-isoxazole, 4-isoxazole, 5-isoxazole, 4-isothiazole, 4-1,2,3-triazole, 4-thiadiazole, 5-1,2,3-thiadiazole, 4,5-dihydro-4-pyrazole, 2-pyridine, 3-pyridine, 4-pyridine, 1,4-oxathiine, 3,4-dihydro-5-pyran, 2,3-dihydro-1,4-oxathiine, and 2-pyrazine;

wherein:

Het is substituted in the ortho position by at least one substituent linked by a carbon atom and selected from the group consisting of a halogen atom, a $C_1$-$C_8$-alkyl, and a $C_1$-$C_8$-halogenoalkyl having 1 to 5 halogen atoms; and Het is substituted in any other position by a substituent selected from the group consisting of a halogen atom, a $C_1$-$C_8$-alkyl, an amino group, a $C_1$-$C_8$-alkylamino, and a di-$C_1$-$C_8$-alkylamino.

* * * * *